United States Patent [19]

Stapleton

[11] Patent Number: 5,188,963
[45] Date of Patent: Feb. 23, 1993

[54] DEVICE FOR PROCESSING BIOLOGICAL SPECIMENS FOR ANALYSIS OF NUCLEIC ACIDS

[75] Inventor: Marilyn J. Stapleton, Durham, N.C.

[73] Assignee: Gene Tec Corporation, Durham, N.C.

[21] Appl. No.: 438,592

[22] Filed: Nov. 17, 1989

[51] Int. Cl.⁵ ................ G01N 33/559; G01N 33/561
[52] U.S. Cl. .................................. 435/299; 435/281; 204/182.6; 204/182.8; 204/299 R; 422/104; 436/515; 436/516
[58] Field of Search ............ 422/56.58, 69, 101, 422/102, 104; 436/177, 178, 515, 516; 435/287, 299; 204/182.6, 182.8, 182.9, 299 R

[56] References Cited

U.S. PATENT DOCUMENTS

| | | | |
|---|---|---|---|
| 3,915,647 | 10/1975 | Wright | 436/169 |
| 4,136,007 | 1/1979 | Fujimori | 204/299 R |
| 4,142,960 | 3/1979 | Hahn et al. | 204/299 R |
| 4,260,392 | 4/1981 | Lee | 422/56 |
| 4,314,897 | 2/1982 | Monte et al. | 204/299 R |
| 4,633,195 | 7/1987 | Mullis et al. | 435/6 |
| 4,683,202 | 7/1987 | Mullis | 435/91 |
| 4,695,548 | 9/1987 | Cantor | 435/179 |
| 4,709,810 | 12/1987 | Mayes | 206/205 |
| 4,828,669 | 5/1989 | Hellman, Jr. | 204/299 R |
| 4,861,712 | 8/1989 | Bartl | 422/58 |
| 4,929,329 | 5/1990 | Danby et al. | 204/299 R |
| 4,978,507 | 12/1990 | Levin | 422/100 |

*Primary Examiner*—Robert J. Warden
*Assistant Examiner*—Theresa A. Trembley
*Attorney, Agent, or Firm*—Olive & Olive

[57] ABSTRACT

The matrix carrier is a hinged compartment facilitating automation of DNA- and RNA-based diagnostics and genetic surveillance and detection. Specimens are embedded in a matrix in the carrier. The matrix is then treated by one or more of the techniques such as amplification, electrophoresis, and hybridization as selected for the desired analysis and then the sample is treated to detect the cellular component.

12 Claims, 3 Drawing Sheets

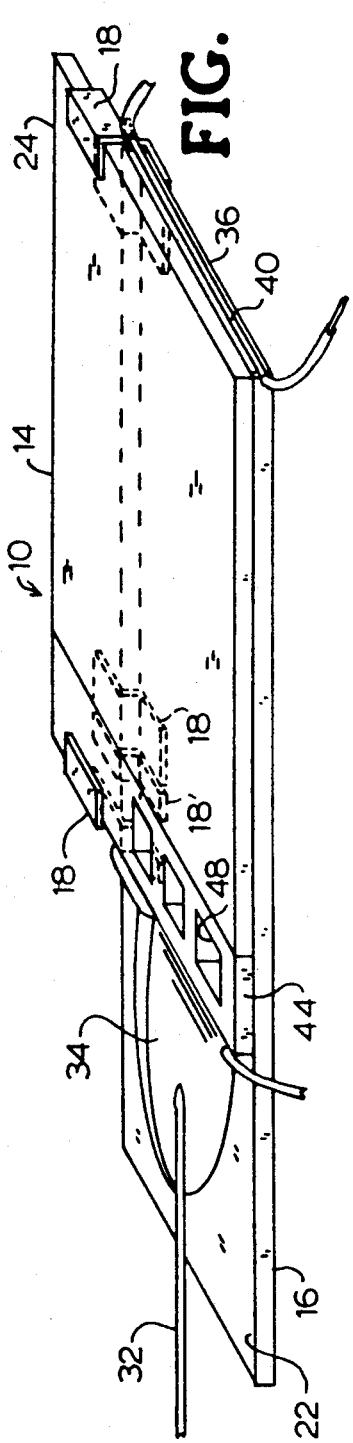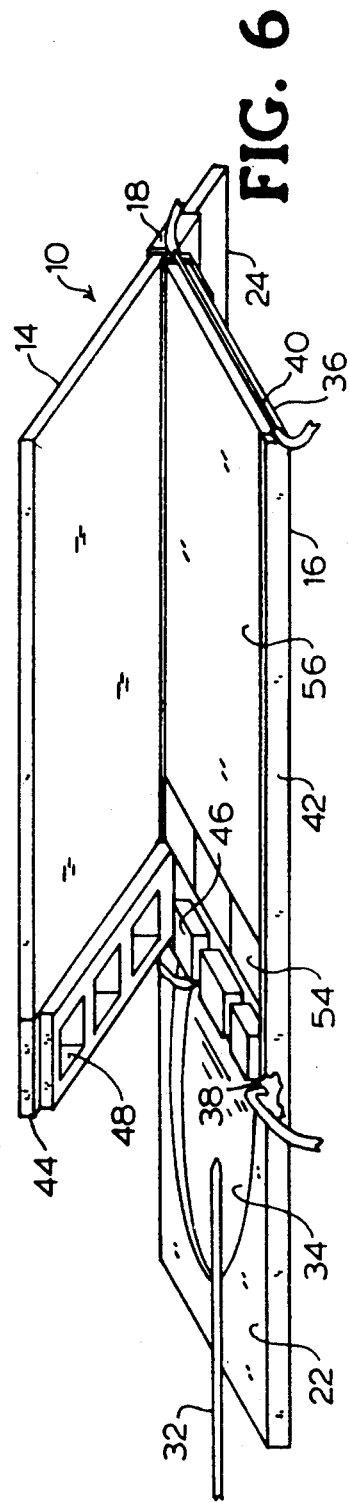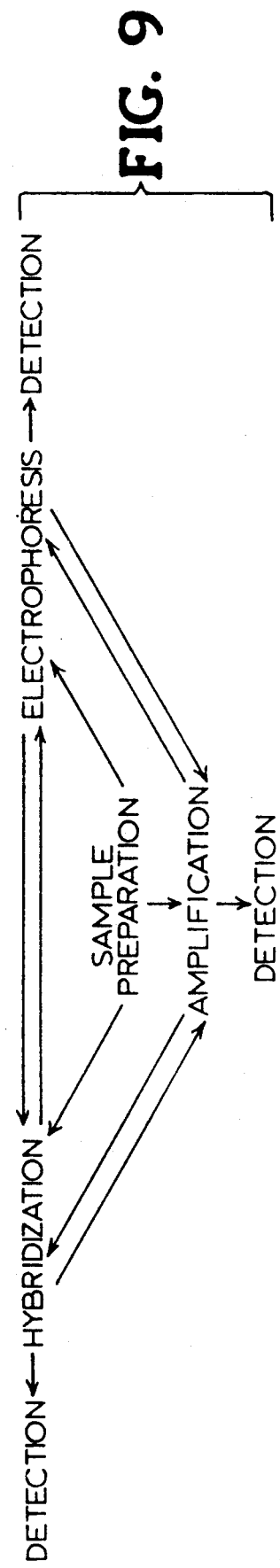

DEVICE FOR PROCESSING BIOLOGICAL SPECIMENS FOR ANALYSIS OF NUCLEIC ACIDS

BACKGROUND OF THE INVENTION

1. Field of the Invention

This invention relates to a device for use in automating the detection of target nucleic acid sequences in biological-containing samples. The device described herein is for use with an automated process, including a fluid-delivery system and a thermal reaction chamber, as is described in co-pending U.S. patent application Ser. No. 07/227,348. The disclosure of the co-pending application is hereby incorporated herein by reference.

2. Description of the Related Art

Devices for receiving biological specimens for diagnostic purposes are varied and adapted to the methods of detection. The devices may take the form of tubes for liquid specimens, flat surfaces such as glass slides suitable for microscopy, microtiter dishes, Petri dishes and cubes containing growth medium, or filters made of various materials to which cell and viral components will adhere.

These specimen samples are then treated in such a way as to indicate either the presence or absence, or quantity, of a specific biological entity Test reagents may either be preapplied to the device or added in series after the specimen is present. Test results are read manually by a technical person or automatically with instrumentation specifically designed for that assay. In some instances the specimen is diluted with a diluent, or an aliquot of the specimen is removed from the original collecting device and transferred to another vessel at some point in the assay. In some cases physical and chemical means are used to amplify the signal of the assay for greater sensitivity Some assays require extraction or separation to isolate a specific component from other parts.

In DNA-based diagnostics the sequence specificity of base-pairing or enzymatic or other types of cleavage is exploited. The linear sequence of nucleotides in double-stranded DNA molecules forms the basis of replication of the genetic code. Hybridization is the binding of two single-stranded DNA strands whose base-pairing sequences are complementary. Temperature and salt concentration affect the stringency of these base-pairing matches A change from high stringency to low stringency can cause the same DNA probe to be either exquisitely specific to detect a particular target or less specific and detect a group of related targets.

In some instances the sizes of DNA fragments, produced by restriction endonuclease digestion or by amplification of a target sequences between primer pairs, are used to make a DNA-print for individual identification or aid in diagnosis of a genetic disease, cancer or infectious disease. For example, electrophoresis may be used to size-fractionate different-sized nucleic acids which have been specifically cleaved or whose native length puts them in a distinguishable size-length class. In the electrophoresis method, a current is applied to DNA loaded at the cathodal end of a gel matrix, which causes the DNA to migrate towards the anodal end of the matrix. The electrophoretic mobility of DNA is dependent on fragment size and is fairly independent of base composition or sequence. Resolution of one size class from another is better than 0.5% of fragment size (Sealy P. G. and E. M. Southern. 1982. Gel electrophoresis of DNA, p. 39-76. In D. Rickwood and B. D. Hames (EDS.), Gel Electrophoresis of Nucleic Acids. IRL Press, London). This reference and all other publications or patents cited herein are hereby incorporated by reference.

Electrophoresis methods thus require a vessel to hold the matrix material and the biological specimens to be subjected to electrophoresis. Such vessels may mold the gel matrix during its formation and may hold it during processing.

Diffusion of reagents is faster where the ratio of the matrix surface area to matrix volume is greatest as in thin, flat matrices. Likewise, electrophoresis of macromolecules requires less voltage and is faster in ultra-thin matrices or tiny (glass) capillaries. In these aqueous matrices, the vessel is necessary to prevent evaporation and to add strength in handling. Existing vessels that enclose matrices impede rapid diffusion of reagents and molecular probes. Once the existing vessels are taken apart in processing, they cannot be put back together to continue automated processing.

Accordingly, the invention aims to provide a vessel for the individual specimens to be contained.

Yet another object of the invention is to mold matrix material which is to contain the specimen.

A further object of the invention is to carry the specimen in transport from the point of collection to the processing point.

A further object of the invention is to provide support of the specimen, embedding it in a matrix for automated processing.

A further object of the invention is to provide a convenient way to make the particles containing target nucleic acids of a specimen in a matrix available for optimal signal detection.

A further object of the invention is to allow for saturating specimens quickly with a series of solutions or for drying them automatically.

A further object of the invention is to concentrate specimen nucleic acids, or amplified products thereof, for detection of their presence.

A further object of the invention is provide a barrier to evaporation of solutions during processing.

A further object of the invention is a mechanism to change its configuration during processing of the specimen to adapt to processing conditions.

A further objective of the invention is to provide support for reading the test results.

A still further object of the invention is to permanently store the nucleic acids present in the specimen for possible retesting and serve as a permanent record of the test, if an archival record is desired.

Other objects and advantages of the invention will be more fully apparent from the ensuing disclosure and appended claims.

SUMMARY OF THE INVENTION

In a broad aspect, the device of the invention comprises:
 a top piece and a bottom piece, said bottom piece having a matrix holding area, said top piece having a closed position;
 said top piece and said bottom piece hinged together along a first side of said bottom piece, said top piece having a first area that extends beyond said first side, whereby downward pressure on said first area causes the top piece to hingedly move away from the bottom piece and upward from the closed position to an open position; and said bottom piece having an overlap area on a second side of said bottom piece, said overlap area extending beyond said top piece, said overlap area having a fluid receiving depression, whereby fluid added to said fluid receiving depression may diffuse into matrix material placed in said matrix holding area.

The bottom piece and top piece are preferably parallel to each other except where the matrix is not of a uniform thickness.

In more detailed aspects of the device of the invention, the "first side" of the bottom piece may be an end or a long side of the preferably elongated bottom piece. Thus, in a first embodiment of the carrier device of the invention the top piece is hinged to the bottom piece along a short edge of said bottom piece and towards the short edge of the top piece, and said first side is opposite and parallel to said second side.

In a second embodiment of the device invention, the top piece is hinged to the bottom piece along a side edge of said bottom piece and said top piece, and said first side is perpendicular to said second side.

The method of the invention utilizes the device of the invention. The sample to be analyzed for the presence of a particular DNA component (or RNA or polypeptide moiety) is suspended in matrix material placed in the matrix holding area of the device. Any one or more of the following steps may then be performed on the matrix and suspended sample, depending on the sample and the results desired: (a) removal of undesired components, e.g. cell wall material, proteins, etc., (b) amplifying a desired nucleic acid component in the matrix material; (c) applying an electric current to the matrix material; and (d) hybridizing a labeled probe to a desired component. Subsequent steps known in the art may be used to detect the particular component in the matrix, or the component as amplified and/or labeled in the matrix.

The device of this invention facilitates automation of DNA-based diagnostics and genetic surveillance and detection. Although the discussion and examples herein are directed primarily to DNA analysis, it is clear that the device of the invention may be used with RNA with equal facility. The device of the invention serves as the specimen container. It can also serve as a mold for embedding a specimen in its matrix. It serves as a specimen holder for manual and mechanical handling and transport. The device serves as an individual archival record for each sample specimen. The sample nucleic acids are preserved in such a way that they may be tested more than once, or the sample may be analyzed for the presence of other nucleic acid targets.

Its parts are configured to open and close via a hinge connection. The closing mechanism may be incorporated into the automated instrument (for automatic gene processing and detection according co-pending application Ser. No. 07/227,348), which opens and closes the hinged parts. Said application is incorporated herein by reference. The invention may also be opened and closed manually.

One way the invention is different from other diagnostics is that in the invention nucleic acids in specimens, may be dispersed randomly in the matrix, and detected as individual targets in the specimen The significance of this format is that target nucleic acids in the dispersed cells or viral particles are enumerated in order to quantify the number of cells or viral particles containing the suspected target DNA. A given degree of amplification of target DNA in a matrix will distinguish locations that represent a few copies of original target from many copies of target. The difference in amplitude of these signals, and construction of a total signal by summing individual signals, reflects a more accurate quantitative answer for each specimen as opposed to measuring a single amplitude for total signal of each specimen. In addition to improving measurement of signals over background noise, the method is useful to distinguish individual particles/cells having a few copies of a target DNA from those with many copies. This information can be predictive (1) in cancer when in vivo gene amplification means a more aggressive malignancy or (2) in viral infections to distinguish latent from active infection.

DNA sequences are excellent molecular probes because of the complementarity of primer and probe sequences to target DNA for the purpose of amplification and hybridization. Similarly the recognition sites of restriction endonucleases are DNA-sequence specific. Restriction fragment length polymorphisms (RFLP's) are the result of restriction endonuclease cleavage and require electrophoretic size fractionation. Detecting a particular sequence variation may indicate individual identity, disease susceptibility or disease state.

The purpose of the electrical current in electrophoresis within the device of the invention is to fractionate and concentrate the macromolecules by size. In the case of nucleic acids, either specific restriction endonucleases, ribozymes (non-protein RNA molecules that cut and resplice RNA into genetic messages) or polymerases may be introduced into the gel matrix to act upon the nucleic acids, which are selectively embedded. "Selectively embedded" means that the nucleic acids of specimens are trapped and other cell components are washed away. Experiments have shown DNA sequences of a few hundred nucleotides or more remain essentially immobilized during amplification and hybridization conditions in given matrix materials while allowing short oligonucleotides, mononucleotides or enzymes to diffuse as necessary. The endonucleases break linear DNA into restriction fragment polymorphisms. Polymerase molecules, together with DNA primers, are used to expand a selected DNA or RNA fragment population. With addition of electrical current, the fragments move through the gel matrix toward the anode, according to their size. Subsequent staining or hybridization within the matrix and carrier enables the identification of specific band patterns. Amplification products may be identified by electrophoretic separation and non-specific DNA staining; but in some cases hybridization probes are necessary to distinguish them from spurious amplification products which cause ambiguities.

Electrophoretic mobility of specific DNA restriction fragments, RNA messages or amplified nucleic segments are then compared with those similarly treated from another specimen For example, specimens from two or more individuals may be compared for paternity identification. Forensic specimens may be compared to specimens from suspects. Family groupings may be compared for markers of genetic disease. Tumor specimens may be compared to standards for classification.

The electrophoretic character of this device is different from other electrophoresis equipment in that the macromolecules in the matrix are automatically processed before, after or in between electrophoretic phases. Different fluid treatments are applied automatically in series to the matrix carrier. The ability to automatically change the solution saturating the matrix heretofore was not possible. The instrument in my co-pending patent application provides processor-controlled fluid delivery to individual matrices. An equivalent electrical current is supplied to each matrix carrier in each rack by design of the circuits.

Previously, multiple specimens were grouped in the same matrix for simultaneous electrophoretic comparison. In this invention, specimens contained in each matrix are processed and compared with both a standard built into each matrix and a standard matrix processed with each instrument operation. A matrix carrier manufactured with quality control standards is another advantage of the automated system. The electrical resistance of each matrix will be reproducible when it is saturated with standard buffer. Advantages of the automated handling and separating of specimens into multiple matrices are (1) standardization of accurate assay results (2) less technician skill and less technician preparation and handling time required and thus lower test cost (3) more convenient sample collection and (4) less human error in switching samples or labels. Current methods require a technician to prepare a sample and transfer it to another container or a gel together with other specimens. A specimen may go through several container changes during processing, and each container change is a possible source of error in identifying a patient specimen or sample source. The matrix carrier in this invention contains the patient specimen or sample throughout the entire processing.

In standard electrophoresis the prepared sample is manually loaded in the gel for electrophoresis, and the gel, or the nucleic acids in it, are manually handled for hybridization and detection. The feature of the matrix carrier of the invention is that the physical and chemical handling of it is automated within the instrument. Other gel matrices molded in a carrier are removed from the carrier for staining or further processing. This carrier is unique in that it can be opened and closed mechanically by the instrument in coordination with the fluid and air flow systems in the thermal chamber of the instrument. This feature allows the genetic specimen to undergo further treatments without transfer to another vessel.

Furthermore, the automated system represents versatility in applications. A unique matrix carrier is intended for each specific diagnostic or DNA identification test. Matrix size and composition will be adapted to perform a particular kind of assay. Racks are designed to hold matrices of the same design. The same basic instrument design will hold any rack configuration and accommodate processing for any of the tests It is also clear that instead of or in addition to using the carrier for electrophoretic separation of DNA or RNA, the carrier may be used for analysis of sample proteins using standard electrophoretic techniques or in situ histochemistry.

Sequence-specific nucleic acid identification depends upon one or more of three fundamental methods: amplification, hybridization and electrophoresis, all of which may be performed using a matrix carrier according to an embodiment of the invention. The automated system for DNA-based diagnostics herein incorporates one or more of these methods in a given order depending upon the nature of the specimen and the quantity of nucleic acid in a particular type of specimen Microprocessor-controlled processing starts with a sample preparation phase. Lysing and deproteinizing treatments are performed automatically to prepare the sample specimen after it is incorporated into the matrix carrier and loaded into the instrument as discussed in co-pending application Ser. No. 07/227,348. The application of treatments that follow are programmed to perform methods appropriate and prearranged for a batch of similar matrix carriers.

As illustrated in the schematic of FIG. 9, the automated system has great flexibility. After sample preparation any one of the three fundamental methods are performed first: amplification, hybridization or electrophoresis. Detection of the sequence-specific nucleic acid target may occur after treatments for any one of the methods. A particular test can involve one, two or all three methods before detection, in any order.

The invention includes any possible coating of the carrier surfaces with selected biomolecules, natural or synthetically-manufactured, by chemically attaching them to surfactants which normally adhere to the carrier material. For carriers made of glass, a known (standard method of binding biomolecules is with sulfonyl chlorides (Nilsson et at., In W. B. Jakoby (Ed.) Methods in Enzymology, Vol. 104, 1984, Academic Press, Inc., Orlando, Fla.). For carriers made of polypropylene or polystyrene, chemical attachment may be by hydrophobic binding to their phenyl groups. The purpose of preadhering molecules to the carrier is to facilitate the processing of genetic detection.

For a fuller understanding of the nature and objects of the invention reference should be made to the following detailed description taken in connection with the accompanying drawing figures.

BRIEF DESCRIPTION OF THE DRAWINGS

FIG. 5 is a perspective view of a second embodiment of the invention in a closed position.

FIG. 6 is a perspective view of the second embodiment of the carrier of the invention in an open position showing a side hinge and subsections of a matrix.

FIG. 9 is a schematic diagram showing some of the various analyses and methods for which the invention may be used.

DETAILED DESCRIPTION OF THE INVENTION AND PREFERRED EMBODIMENTS THEREOF

Figure 1:
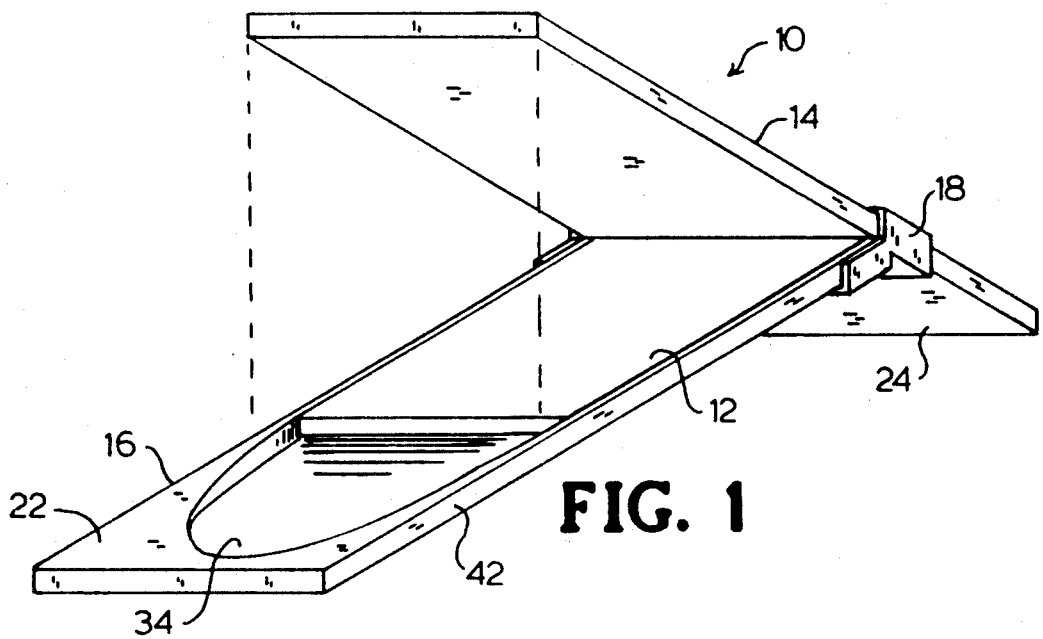
FIG. 1 is a perspective view of a first embodiment of the carrier of the invention in an open position
Figure 2:
FIG. 2 is a side view of the first embodiment of the carrier of the invention in a closed position
Figure 3:
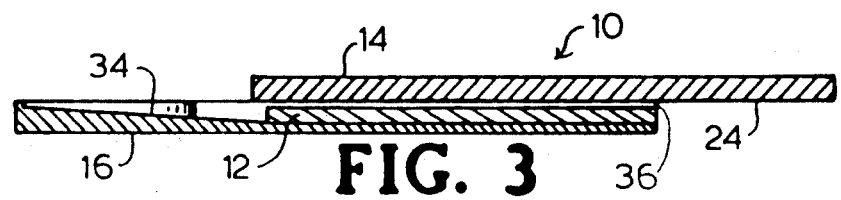
FIG. 3 is a side view of the first embodiment of the carrier of the invention with carrier edge removed showing the matrix space and the channel
Figure 4:
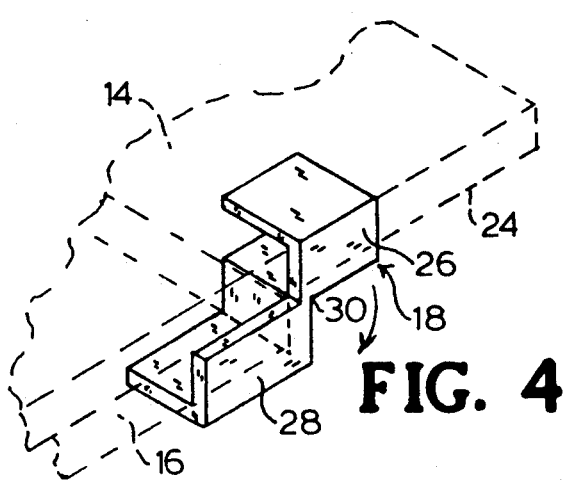
FIG. 4 is a perspective view of a hinge of the first embodiment.

The invention broadly comprises a carrier 10 and a matrix 12 capable of containing biological specimens The carrier 10 is composed of an upper rectangular piece 14 and a lower rectangular piece 16 hinged together; which, when folded, encase the matrix 12 and, when unfolded, expose one surface of the matrix 12.

Two embodiments of the invention are depicted in the figures. Both embodiments may have the electrophoresis electrical contacts, multiple matrix sections and subsections, but for ease of depiction, these variations are not shown in both embodiments.

In a first embodiment (FIGS. 1-4) the hinges 18 are along a shorter side of the lower rectangular piece 16, while in the second embodiment (FIGS. 5-7), the hinges 18 are along a portion of a longer edge of the lower rectangular piece 16. Having the hinge 18 along a longer side portion of the lower piece 16 (second embodiment) is valuable for electrophoresis, where a longer matrix is preferred. Such a side hinge arrangement allows a longer, narrower matrix while requiring less overhead space for opening the carrier than an elongated cover for a carrier that was hinged at an end would require.

The edges of the two pieces 14 and 16 are juxtapositioned to overlap each other so that in the first embodiment (FIG. 1) the upper piece 14 overlaps and extends beyond the lower piece 16 at the end having the hinge 18, and the lower piece 16 extends beyond the upper piece 14 at the end of the carrier 10 that is not hinged In the second embodiment (FIG. 5), the upper piece 14 extends beyond the lower piece 16 at the hinged side of the lower piece 16, and the lower piece 14 extends beyond the upper piece 14 at an edge perpendicular to the edge having the hinge 18.

The lower overlap 22 on the lower piece 16 functions to receive fluids which may diffuse into the matrix 12 whether the invention is in the closed or open position. The upper overlap 24 of the upper piece 14 functions as a lever end to open the invention. Mechanical pressure applied to the upper overlap 24 lifts the upper piece 14 away from the matrix 12, which rests on to the inner surface of the lower piece 16.

Each hinge 18 (FIG. 4) in the first embodiment preferably comprises an upper portion 26 grippingly engaging the upper piece 14 of the carrier and a lower portion 28 attached to the lower piece 16. The means of attachment may be glue or other known means of attachment. A flexible bend area 30 located between the upper portion 26 and the lower portion 28 enables the hinge movement and the opening and closing of the carrier 10. The hinge 18 may be made of flexible plastic, or may be made of a rigid material such as a plastic or metallic alloy, except in the flexible bend area 30. Preferably such a hinge is attached at each side of the carrier 10. Although the carrier is described as comprising separate pieces, it is equally possible that the carrier may be molded as one piece with a "living" plastic hinge connecting the portions or that two or more components of the carrier may be molded together.

Treatment solutions from fluid lines 32 in the device of the co-pending application flow or drip into channel(s) 34 on the lower piece 16 and diffuse into the matrix 12. The fluid system as described in my co-pending patent application delivers measured volumes from one of multiple reservoirs through a common line either in a continuous or pulse mode at a selected flow rate. Fluid application is also important in opening and closing the carrier halves 14 and 16. Application of a fluid volume at the time of opening releases surface tension between the upper piece 14 and the matrix 12. This action reduces the mechanical force required to separate the upper piece 14 from the matrix without disturbing the matrix 12. Application of fluid to the matrix 12 prior to closing the carrier pieces 14 and 16 leaves a liquid film between carrier piece 14 and the matrix 12 upon closing. Closure of the carrier 10 at the hinged joint 18 brings the surfaces that are closest to the hinge 18 together first and gradually those farther away from the hinge 18 make contact. The wave-like closing action smoothes out the bubbles whose presence may cause aberrant test results.

The fluids from channel 34 saturate the matrix 12 and fill the space between matrix 12 and the upper half of the carrier 14, and excess liquids may exit at the opening(s) 36 between the hinged pieces 18. Collecting troughs on the racks and the shelf below the racks within the instrument provide for fluid disposal (not shown). Any opening(s) along the edge are plugged during addition of the matrix material to the carrier 10 when the carrier is being prepared for use until after the matrix 12 has been formed. Taping the opening(s) may be used to close them, but other means of temporarily covering the opening are possible. The tape or other fastener is removed when the carriers 10 are loaded in a rack, or a sealed barrier over the opening(s) may be broken by the opening or closing action of the carrier pieces 14 and 16.

Opening 36 between the hinges 18 or an open side or end of the matrix 12 also allow electrical contact with the matrix material. The electrical contacts 38 and 40, in each embodiment and shown for the second embodiment in FIGS. 5 and 6, permit a constant or deliberately variable electrical current to flow through individual matrices in order to optimally resolve different size classes of macromolecules. A coating with negatively charged groups such as Nafion TM (DuPont Co., Wilmington, Del.) on the lower surface of the upper carrier half 14 and/or the upper surface of the lower carrier half facing the matrix 12 may be used to help reduce electroendosmosis, in which cations in aqueous fluids and hydrogels tend to flow toward the cathode.

The carrier pieces 14 and 16 may be made of glass or plastic or combinations thereof, sheets of polymer (such as polyetherimide, Ultem ®, General Electric, Pittsfield, Mass.) or metallic alloys. Carriers used for assays involving electrophoresis are made of non-conducting materials in order that current flows through the matrix and not the carrier. Parts of the carrier may be made of optically clear material for scanning the matrix.

The matrix 12 is preferably a semi-solid material made with agarose or acrylamide or similar polymer, or mixture thereof, that incorporates several times its weight of an aqueous solution (hydrogel). A liquid specimen or specimen mixed with a liquid diluent may be added to the carrier at channel 34, or into subsections 48 directly, from where it either combines with a liquid matrix 12 or diffuses into a pre-formed dehydrated matrix or a subsection thereof. Application of heat or a polymerizing agent incorporates the specimen into the matrix 12 or subsection thereof, forming a gel matrix with embedded specimen. The gel matrix may be hydrated or not before loading its carrier in the instrument. If dehydrated in storage or transport, the gel matrix material is rehydrated with fluid treatments from the fluid lines 32 of the instrument. A rehydrated matrix, preferably ultra-thin (less than 500 micrometers thick), facilitates diffusion of small molecules and retention of larger ones, quicker electrophoretic resolution and better detection of signal.

The carrier 10 may be molded to have edges 42 or the carrier halves 14 and 16 may have edge pieces fastened to them. The edges 42 are formed in order to enable molding of the matrix material in a space between the upper and lower carrier surfaces 14 and 16. The space between carrier surfaces 14 and 16 may diverge from one end to the other by placing wedge-shaped edges 42 along the sides in order to form the matrix material thicker at one end (not shown). Such a wedge-shaped matrix may be made by pouring molten matrix material into a wedge-shaped enclosure formed between the upper and lower carrier surfaces and bounded by edges 42. The purpose of the wedge configuration is for increasing the electrophoretic separation of a wider range of nucleic acid fragment-size classes over less linear space.

Another aid to better resolution of fragment populations is variation of the concentration of the matrix material over the linear path of electrophoresis, i.e., making a gradient gel matrix. When matrix material is preformed on carrier half 14 or 16, it may be applied in a manner to form a concentration gradient and/or wedge across one dimension for better electrophoretic resolution.

Edges 42, and extensions 44 which may overlap the surface of the lower carrier section 16, are molded or fastened to one or both of the carrier halves. Edges 42 and extensions 44 may form molds for matrix materials, with and without added specimen material. They may be designed to mold either matrices 12 of uniform thickness in the space between the upper 14 and lower carrier 16 surfaces or mold subdivisions of the matrices 12 that contain different matrix materials, volumes or concentrations thereof (FIGS. 5 and 6). The edge 42 in FIG. 6 is shown cut away where electrical contact 38 crosses it. The extensions 44 may form molds 46 on the lower carrier section 16 and subdivide the matrix area into smaller subdivisions. The subdivision of matrices on one carrier allows the different matrix sections to include different specimens or standards.

Introducing the specimen into the matrix allows pretreating the specimen within it to prepare DNA in the sample by a standard method of Smith, Klco and Cantor (1989, In K. Davies (Ed.), Genome Analysis-A practical Approach, 1989, pages 41-72, IRL Press, Oxford) or by variations of a standard method. In a multisection matrix, another section of the matrix may be pre-formed on the carrier and accept DNA molecules transferred to it from the initial matrix via electrophoresis. The purpose of varying materials, or the volume and concentration thereof, in submatrix sections on the same carrier is to optimize conditions for a specific method For example, polyacrylamide gel reagents may be introduced, dried and enclosed in one section of the carrier during manufacture. Later, the sample is mixed with liquid agarose and added to the matrix carrier 10 filling subsection spaces 48 and forming subsection 46. After sample preparation treatments and subsequent drying of the agarose matrix in subsections 46, the carrier 10 is opened and electrophoresis buffer applied to all matrix sections. The nucleic acids (or proteins) are electrophoretically transferred from the agarose to the acrylamide matrix (or an intermediate matrix in subsections 54) for a processing step for which acrylamide is better suited than agarose.

The first matrix the specimen encounters may serve to cleanse it. Drying and rehydrating this matrix reduces total volume and thus concentrates samples. Electrophoretic movement of macromolecules from the concentrated first matrix into the second matrix has the effect of loading a more concentrated sample onto the second gel, i.e., more sample target molecules per unit matrix. The more concentrated the macromolecules are when starting electrophoresis, the more easily detected they are after electrophoretic separation due to a narrower band width. The process of this invention overcomes the difficulty of loading enough sample per unit volume on the thin gels. Our research has found that samples migrate from a dried gel to a second matrix.

Research shows further that an added advantage of using a dried matrix is that macromolecules migrate slower in a dried and rehydrated matrix because the pore size is changed by effectively increasing the matrix substance concentration in the hydrogel. We have also observed the percentage shrinkage of a dried and rehydrated flat hydrogel is several times greater in its thickness than in its length or width.

Thus, the advantages of a dried and rehydrated hydrogel are that: (1) it may be more easily manufactured with a lower concentration of matrix material because later drying will increase the concentration; (2) it may be stored dry; (3) the thinner gel may be rehydrated with less buffer volume than a thicker gel; and (4) the thinner gel that results from the drying and rehydration allows better signal detection than a thicker gel. While other hydrogels may be dried before use, this invention permits automatic changes between alternate drying and saturating processes by opening and closing the carrier without removing the matrix or carrier.

The extensions 44 may be raised after the matrix sections are molded. The same mechanism (manual or mechanical, as discussed above) that opens the carrier halves 14 and 16 may serve to remove the extension sections 44 from the matrix 10. When the carrier halves 14 and 16 are opened at the hinge joint 18, the extension 44, which was separating two or more submatrices on the carrier, is no longer positioned between the submatrices. Gel-to-gel or gel-liquid-gel contact allows the parallel transfer of nucleic acids from one submatrix to another by electrophoresis. In the second embodiment, the extension 44 may be opened separately from the opening of carrier halves 14 and 16. Thus, gel matrices on the same carrier may receive isolated treatment or be treated together with any other.

The purpose of two or more matrix sections is to separate functions or samples within one carrier. It is useful when two or more patient specimens are compared in the same carrier or when one matrix section serves one function and the second matrix section serves another function. Examples of different functions are: (1) cleansing nucleic acids in a specimen from interfering biological material; (2) amplifying the nucleic acid fragments; (3) hybridizing a labeled probe to the nucleic acids; (4) fractionating nucleic acids according to size by electrophoresis; (5) comparing an internal standard on the matrix with an unknown; and (6) comparing band patterns to indicate related individuals.

The racks (not illustrated) may hold a number of matrix carriers and are designed in such a way that they position each of the matrices at the opening of a fluid line 32 for fluid delivery from fluid reservoirs as discussed in my co-pending application. The racks are designed to fit into the instrument's thermal chamber. The racks may support the carrier-matrices 10 in any designated plane, horizontal, vertical or diagonal. Tilting the carrier may serve the purpose of increasing the rate of fluid flow when necessary.

The design of racks in which electrophoresis is used will position the matrix in such a way that the matrix completes an electrical circuit. This optional feature that may be incorporated into the automated system of the co-pending application for use of the instant invention is the positioning of electrodes on each rack of a plurality of racks holding the matrix carriers in such a way that applied current can pass through each matrix saturated with an electrical conducting buffer. Positive and negative connections are located on opposite ends of each matrix and connected via contact leads to positive and negative terminal blocks on the rack (FIG. 8).

Figure 8:
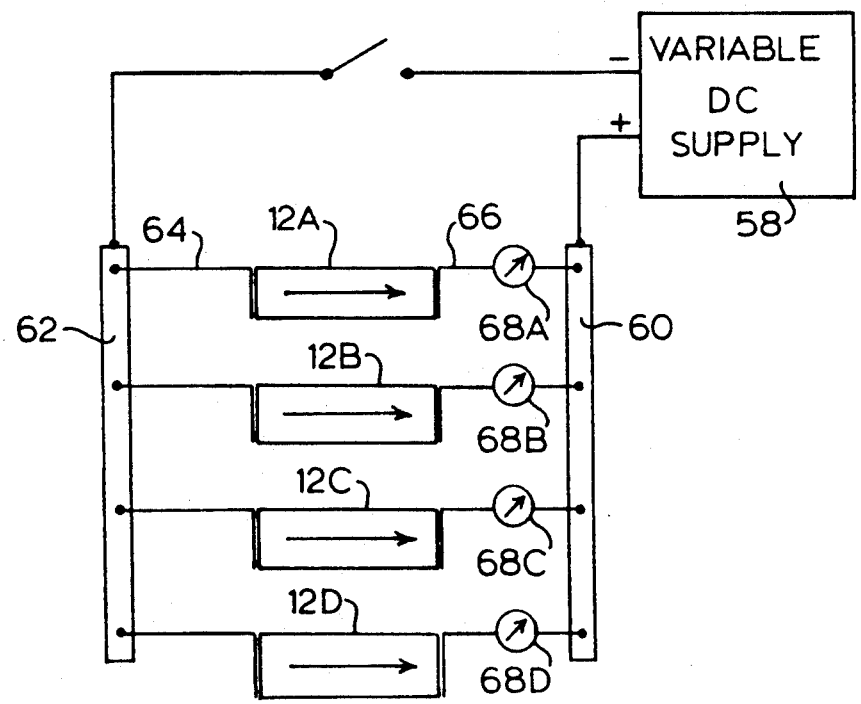
FIG. 8 is a schematic drawing of an electrical circuit closed by a matrix.

In reference to FIG. 8, a variable DC supply 58 has its positive side connected to an anode bus bar 60 and its negative side connected to a cathode bus bar 62. Each electrophoretic matrix 12 of which four are illustrated by way of example, labelled 12A, 12B, 12C, and 12D, is connected on one side to bus bar 62 by way of a lead 64 and on the opposite side to bus bar 60 by way of a lead 66. An ammeter 68 is placed in series with each matrix 12 as illustrated.

In use, the variable DC supply 58 as adjusted to provide an appropriate level of DC voltage and individual monitoring of the current through each matrix 12A, 12B, 12C, or 12D is obtained by monitoring the respective ammeters 68A, 68B, 68C, and 68D. Voltage levels are maintained at levels commonly used for electrophoresis. The ammeter can be connected to an alarm (not shown) so the operator may know if the electrical current is too high, as a backup to discover any inadequate matrices, where there is too great a resistance.

The rack has electrical connections fitting into corresponding connections in the instrument when the racks are in position in the instrument. The rack terminal bus bar is thus connected to a power supply in the automated instrument. The invention so equipped will provide an equivalent electrical current through all gel matrices. In such racks electrical connections from the anode bus bar and cathode bus bar lead to each individual matrix-carrier 10, an anode to one end of the matrix and a cathode to its opposite end. Electrical wire connections are appropriately sheathed with insulating material where no current conductance is desired. Interlocks and lid locks will be placed at all points where an operator may inadvertently come into contact with the electric field.

The air flow system built into the thermal chamber is also used to cool the matrix carriers during electrophoresis and prevent uneven heat build-up. The closed position of the carriers during electrophoresis prevents evaporative loss of buffer from the matrices. The fluid-flow line 32 delivers buffers to the channels 34 to diffuse into the matrices as needed for saturating or cooling them.

The same reaction chamber and rack may be equipped with a mechanism (not shown) to exert a force on the lever end (upper overlap 24) of the carrier. A mechanical platform (not shown) may be equipped with auxiliary heat to raise the temperature of the matrix quickly as it contacts the matrix carrier and lower it quickly when contact is released. A mechanical arm may be equipped with an auxiliary fluid line for delivering reagents or solutions to the matrix carrier different from those supplied through fluid lines 32. The same mechanical arm may be so equipped with a scanning device to read all or a portion of the optical differences on the matrix surface. The purpose of the scanner is convert image data from the matrix to a digital form for computer interface. Either the mechanical arm moves between the rack shelves or the rack moves past the mechanical arm.

In the following examples, amplification is defined as a means to biochemically increase the target nucleic acid mass. Target nucleic acid means those molecules containing a designated genetic sequence Separation of nucleic acids by size utilizing electrophoresis is performed in a hydrogel supplied with an electrical current. Hybridization refers to the binding of complementary nucleic acids sequences, one partner of which carries a label whose signal can be detected. If amplification is used alone or follows hybridization it is understood that the primers or sequences used in binding targets or nucleotides for amplification may also carry a label.

It is further understood that automated processing begins with sample preparation and ends with the test results of detection. It is further understood that standard reagents and reaction conditions may be used for the various sample treatment steps, such as amplification, electrophoresis and hybridization. The following examples are presented to iterate the ways in which the methods that are diagnostic of nucleic acid sequence-specificity may be interchanged or combined in the processing. In the following examples, the specimens in sections 46 are combined with matrix material which might be agarose; sections 54 are pre-formed in the carrier and may be different compositions to amplify different targets Polymerase chain reaction (PCR) is shown in the preferred method of amplification when amplification is used, but amplification methods are not limited to PCR. Our research demonstrated amplification in agarose gels by PCR with Taq polymerase. The addition of more primer molecules during PCR as they are used retards formation of undesirable primer dimers Although not discussed in detail herein, standard techniques including immuno-staining for analysis of polypeptides or other cellular components in gels may be performed with the device of the invention.

EXAMPLE 1

Matrix and Carrier for Sample Preparation, Amplification and Hybridization

The initial process of sample collection involves randomly distributing specimen in diluent if the sample is too concentrated for analysis, and then combining it with a liquid matrix material or a pre-formed matrix in the carrier.

The order of treatment methods in this example are sample preparation, amplification, hybridization and detection. This application would be used in a diagnostic in which amplification with specific primers yields discrete products from non-target DNA, some of which may even be in the same size class as the target DNA. These products can be discriminated by hybridization from target sequences. In particular, this protocol may be used for detecting proviral sequences of human immunodeficiency virus type 1 or human T-cell leukemia virus type 1 where these other products have been reported (Abbott, M. A., B. J. Poiesz, B. C. Byrne, S. Kwok, J. J. Sninsky and G. D. Ehrlich. 1988. Enzymatic gene amplification: qualitative and quantitative methods for detecting proviral DNA amplified in vitro. J. Inf. Dis. 158:1158-1169.).

If the specimen is a sample from blood or another body fluid, a measured amount may be added directly to the matrix 12 through the channel 34. The matrix carrier 10 is processed by heat or chemicals to embed the specimen in the matrix 12 and render it non-infectious. The matrix carrier 10 is closed during transfer to the instrument site, where it is loaded, along with others, onto a rack and placed in the thermal chamber of the instrument. The fluid delivery system sequentially supplies multiple reagents in series through an individual fluid line 32 to each matrix-carrier. Thus, a lysing-sample preparation solution from the fluid line 32 flows into the channel 34 on carrier section 16 and diffuses into the matrix 12 and is used to remove non-nucleic acid components in the sample. The carrier is mechanically opened as the solution reduces surface tension between the upper matrix surface and the carrier piece. The final solution of sample preparation rinses away previous solutions and forced, heated air of the thermal chamber dries the matrix with the carrier still open.

The amplification solution and reagents are then added through the fluid line 32 to rehydrate the matrix. The carrier closes during amplification temperature cycling to prevent evaporation. After amplification the carrier opens to facilitate rinsing and adding hybridization solutions. The carrier closes during hybridization to an enzymatically-labeled nucleotide probe and opens again for the stringency washes, and subsequent addition of substrate and buffers for detection. After substrate development the carrier closes for reading by a scanning detector. One possible detector may be an optical array for measuring transmitted or reflected light differences that distinguish positive signals over background noise. The scanning is not limited to detecting enzymatic activity on a chromogenic substrate, but other labels, such as fluorescence may be used.

Data from amplification and hybridization experiments with the matrix covered and uncovered indicate opening and closing of the carrier is critical to facilitate either rinsing or drying of the matrix in the open configuration and controlling evaporative loss during reaction periods in the closed position. Experiments which were performed in a covered or closed matrix had retarded diffusion of treatment solutions, and retarded rinsing and drying the matrix. Water evaporation from the matrix in an open carrier leaves behind more concentrated solutions which affects desired enzymatic activity. If the matrix dries out during hybridization, signal noise increases. A carrier-fluid-matrix interface at the surfaces of the matrix appears to be important for molecular diffusion when the carrier is closed. One reason drying the matrix before amplification and hybridization is important is that drying causes the matrix to shrink and consolidate the nucleic acid molecules into a smaller volume. Agarose does not rehydrate to its original volume so less rehydrating solution is required and thereby fewer primer or probe molecules are needed to maintain an adequate molarity A dried agarose matrix soaks up reagents like a sponge, hastening diffusion of necessary biomolecules. The ability to open and close the carrier during processing as allowed by the carrier of the invention has been found to serve the above multiple purposes.

In the case of a genetic disease caused by a single base mutation such as cystic fibrosis, the purpose of a diagnostic is to determine the presence of mutant alleles either as homozygous or heterozygous genes. Here amplification of the target DNA or RNA means fewer specimen cells are needed. After sample preparation and amplification, hybridization with the appropriate labeled oligonucleotide probes, under stringency conditions which distinguish either the single base-pair match or mismatch, will be sufficient for detecting the disease or carrier state.

EXAMPLE 2

Matrix Carrier Design for Sample Preparation, Amplification and Electrophoretic Separation In this example, the sequence of methods is sample preparation, amplification, electrophoretic separation of amplified fragments, and detection by staining of fragments and scanning resulting bands for interpretation by image analysis software. This example illustrates the value of matrix subsections and racks designed with electrical bus bars leading to each matrix.

Figure 7:
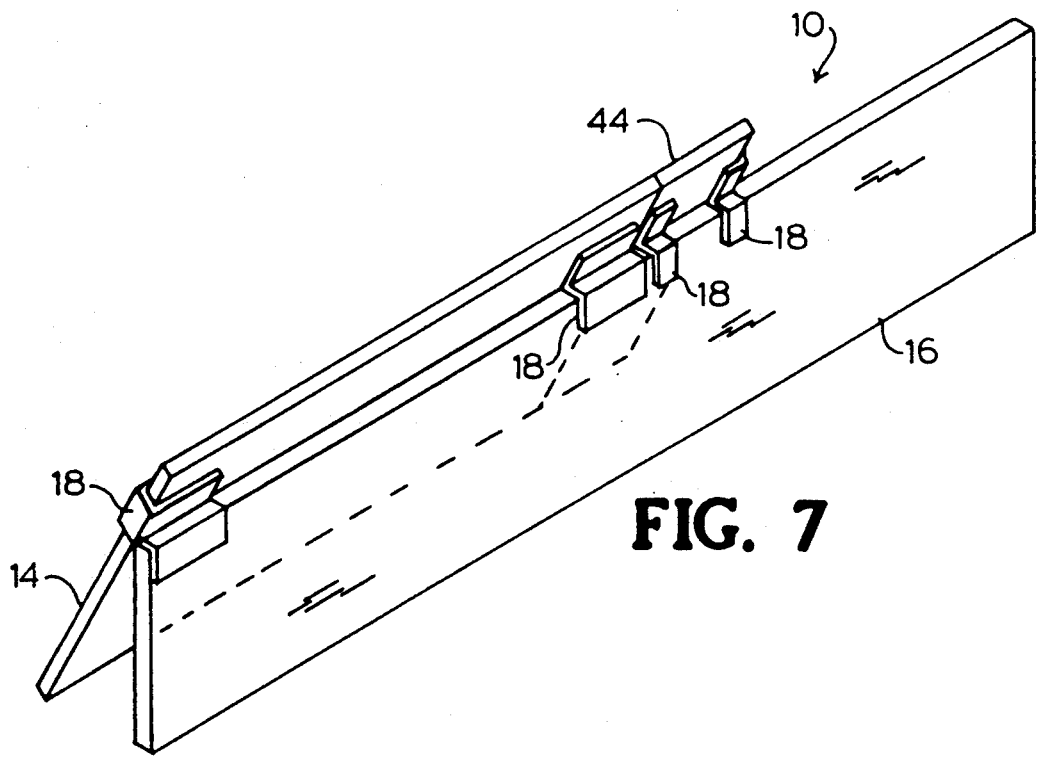
FIG. 7 is a back perspective view of the second embodiment of the invention showing the hinge.

An example of a subdivided matrix is illustrated in FIGS. 5-7. A mixture of specimen and matrix material is added to form subsections 46 of matrix 12. Although three subsections are shown, this amount maybe varied for particular uses. The fluid lines 32 are supplied by the fluid delivery system of the instrument in my co-pending application. Carrier extension piece 44 is raised after the matrix and specimen subsections are set. Sections 46 are treated with fluids from fluid line 32 in order to make nucleic acids from particles/cells in the specimen more available for modification or detection and to reduce interference from non-nucleic acid molecules. The hinged edge of extension piece 44 has an opening(s) in order for fluids collecting around subsections 46 to drain off into troughs on the racks.

The contents of sections 54 and 56 are protected between the carrier halves 14 and 16 in the closed position or by the barriers formed by edge extensions 44. The treatment solutions from the fluid line 32, used for lysing and washing the sample, do not enter the enclosed sections 54 and 56. After sample preparation is complete in subsections 46, the instrument automatically opens the carrier enabling fluid to enter matrix sections 54 and 56. This fluid is an ionic buffer that permits DNA to migrate towards the anode when current is applied.

Current is supplied from leads from the bus bar fastened to the shelves of the rack in such a way that each matrix placed on the rack comes into electrical contact with leads of opposite polarity, and when saturated and current is applied, the matrices close parallel circuits. An electrical current flowing through the buffer-saturated matrix-coated carrier, as shown by the arrows on FIG. 8, causes the nucleic acids from the specimen in sub-sections 46 to migrate into subsections 54.

Preformed matrix subsections 54 may hold different primer sets for amplification of different target fragments in duplicate specimens, or a subsection 54 may contain known DNA standards. These designated primer sets could be immobilized in sections 54 at the time of matrix-carrier manufacture. After the first electrophoresis, the fluid line 32 supplies sections 54 with amplification buffers to supplement what reagents are already incorporated in them. Controlled temperature cycles allow treatments from fluid line 32 to enzymatically amplify a specific target DNA sequence in closed carriers. The carrier may be sealed in manufacture with a polyethylene film to cover matrix sections 54 and 56 and prevent contact with aqueous fluids from channel 34. Once the carrier is opened, the seal is physically separated so that subsequent closing of the carrier allows fluids to be drawn through the carrier halves when closed.

The second application of current allows the DNA molecules, including the amplification products, to migrate into section 56. In cases where primers were reversibly immobilized in the preformed matrix subsections, a treatment step to release them is included. Section 56 is also a preformed matrix of still a different composition. The composition of section 56 is selected to resolve different-sized fragments; the composition and buffers chosen could be as described by Allen et al. (supra) comprising a 5% T wedge rehydrated polyacrylamide gel and discontinuous buffer system. In a discontinuous buffer system a sulfate-leading ion made by adding $H_2SO_4$ in a buffer may be incorporated into the cathodal end of the section 56 matrix and the borate-trailing ion incorporated into the overall section 56. The ions may be supplied by prior incorporation of one into the matrix section with the other supplied by fluid line 32 at the time of electrophoresis. In instances where ionic buffer salts are incorporated in the matrix 56, adding deionized water through fluid line 32 will sufficiently hydrate the matrix to supply the buffer requirements. In other instances buffer prepared at its final concentration is supplied through fluid line 32.

After the electrophoretic separation of DNA fragments, the carrier halves are opened to permit staining solutions to diffuse into section 56 and stain fragments for visualization. The fluid line 32 supplies staining solutions. DNA identification in this case results from comparing bands representing the electrophoretic mobility of an expected target fragment size-class to standards and/or other specimens. In this example all nucleic acids present in the matrix are stained and the preferred method of staining might be silver staining according to the modification of Allen et al. in which polymerase chain reaction amplification products are separated on rehydratable polyacrylamide gels and stained with silver which detects 10 pg/mm band widths (Allen, R. C., G. Graves and B. Budowle, BioTechniques 7:736-744, 1989). The staining process is developed to an optimal level. The carrier halves are closed after staining treatments to flatten the matrix in one plane for scanner reading. A mechanical arm passes the carrier half that is transparent by either movement of the arm or the rack. The mechanical arm might contain an arc light as a light source, lenses for focusing or intensifying light, and an optical array for detecting either transmitted or reflected light. The intensity of the light source and the speed of the pass can be varied to produce the best signal-to-noise ratio and be set to an internal standard matrix before reading the other matrices.

Examples 1 and 2 demonstrate the use of designated matrix carriers in the automated system, the first one being a viral diagnostic test and the second being a DNA identification test. A specialized carrier enables many functions to occur on an individual carrier which is processed automatically along with others in the same fashion. In the second example, closing the matrix halves is critical in protecting a matrix subsection during prior treatment to another subsection and opening is critical in permitting rehydration of a preformed matrix. The fluid delivery system supplies different reagents through a common fluid line to individual matrices. The DNA from the specimen in the second example migrates from one subsection of the matrix carrier to another by electrophoresis. Subsections 46 are thicker than 54 in order to prepare the sample in a larger matrix volume and then concentrate it by drying. Experiments performed with the carrier of the invention demonstrate that fragments will migrate through dried and rehydrated gels to other gel matrices. Fractionating the DNA in ultra-thin matrices results in better signal detection. The matrix subsections of the carrier of the invention have been found to serve the above multiple purposes.

Two matrix carrier designs are described above in detail to illustrate how different types of matrix carriers may be designed to fit the needs of particular DNA-based tests. The following examples are described very briefly to enumerate possible combinations that exist for additional matrix carrier designs.

The automated system as outlined in each of the examples includes sample preparation as the first step and detection (reading and interpreting signal) as the final step. The intermediate steps are defined as those which supply the specificity of nucleic acid sequence to the system and vary among the examples.

EXAMPLE 3

Amplification, Electrophoretic Separation and Hybridization

A variation of Example 2 may be used when electrophoretic band patterns of amplified fragments are ambiguous. Rather than staining all DNA bands for detection as illustrated in Example 2, hybridization with labeled probes permits detection of only those bands having sequence complementarity.

EXAMPLE 4

Amplification, Hybridization and Electrophoretic Separation

A variation of Example 3, in which the order of electrophoresis and hybridization are reversed, may be used when detection of amplification products is improved by electrophoresis after labeled molecular probes have bound to them. The DNA product-labeled probe complex may have a more distinguishable electrophoretic band pattern. Another advantage is that hybridization is more efficient in the smaller volume of matrix subsection than it is in the volume of a larger matrix section into which DNA has been electrophoresed.

EXAMPLE 5

Hybridization

If in Example 1, sufficient components are present in a specimen, amplification may not be required and the detection would require only hybridization to a labeled probe after sample preparation.

EXAMPLE 6

Hybridization and Electrophoretic Separation

One instance where hybridization followed by electrophoresis would be useful is where labeled DNA probes are hybridized to RNA transcripts and the DNA:RNA hybrids produce a fragment size class distinguishable by electrophoresis. Similarly, labeled DNA or RNA complexes may be cleaved at particular recognition sites and electrophoresed to enhance their detection.

EXAMPLE 7

Hybridization, Electrophoretic Separation and Amplification

If, in Example 6, the amount of target is below detectable levels, amplification increases sensitivity of detection and may be performed after hybridization and electrophoresis. .

EXAMPLE 8

Amplification

Amplification that is specific enough for detection without hybridization or electrophoresis is possible. Detection is by measuring the increase in mass of DNA or RNA after amplification. In this case measuring labeled nucleotide incorporation simplifies the assay. Unincorporated, labeled nucleotides may be readily washed away before detection.

Additionally, the more primer sequences used in PCR to amplify more fragments, the more specific is identification of target DNA. There is a dampening effect that limits the number of primer pairs that can be used together, which varies according to the nature of the target and background DNA or RNA. A particular assay may be used in which multiple primer pairs are used to increase the total quantity of DNA in the sample. Duplicate samples are run in parallel on the same matrix as positive and negative controls. The positive controls have primers to amplify a conserved region of specimen DNA that is species-specific and indicates the starting amount of total DNA present in the specimen. Another positive control of known target DNA demonstrates adequate assay conditions. A negative control starts with non-target DNA to indicate possible contamination of assays components.

Specimens that lack primer-binding targets do not increase DNA content and such a test is useful in genetic disease or tumors where deletions of both normal alleles cause a disease state. This test design may also be used to compare the number of copies of a tumorigenic or an oncogenic region with those of a single copy gene in order to quantify the extent to which the gene has been amplified naturally in any given tumor.

EXAMPLE 9

Hybridization and Amplification

The Q-beta replicase method of detection requires hybridization before amplification and may be used in the device of the invention. (Lizardi, P. M., C. E. Guerra, H. Lomeli, I. Tussie-Lune, F. R. Kramer. 1988. Exponential Amplification of Recombinant-RNA Hybridization Probes. Biotechnol. 6:1197-1202.) An oligonucleotide probe is inserted in a RNA that serves as a template for RNA synthesis by the enzyme called Q-beta replicase. The enzyme polymerizes multiple RNA transcripts which include the target sequence.

EXAMPLE 10

Hybridization, Amplification and Electrophoretic Separation

Electrophoretic separation after RNA transcripts are produced according to Example 9 is a way to analyze the integrity of the RNA transcripts. The mobility of the RNA provides verification that the relatively large mass of RNA generated is in the size class of desired recombinant RNA.

EXAMPLE 11

Electrophoretic Separation and Hybridization

Restriction Fragment Length Polymorphisms (RFLPs) are DNA fragments resulting from endonuclease cleavage of genomic DNA whose length varies from individual to individual by virtue of whether the specific recognition site of the endonuclease is present or not at a given location in the genome. After electrophoretic separation of these fragments according to size class using the device of the invention, labeled DNA probes are hybridized to these variable regions resulting in unique banding patterns which identify an individual and the individual's relatedness to other individuals. In some instances the same genetic variation that alters the restriction site also causes an abnormal phenotype and thus determines the disease condition directly. In other instances, linkage relationships are established between a genetic defect and an RFLP allele which acts as a genetic marker. RFLP's are used to identify genetic diseases or predict chances that offspring will inherit a genetic disease. They may also be used to prove or disprove identity in paternity or forensic cases.

EXAMPLE 12

Electrophoretic Separation

Electrophoretic separation in the device without amplification or hybridization may be sufficient to provide useful information. In less genetically complex organisms the electrophoretic banding pattern of endonuclease-restricted total genomic DNA yields strain or species identity. In bacteria, for example, a densitometric scan of these electrophoretic bands can distinguish one kind of bacteria from another.

EXAMPLE 13

Electrophoretic Separation and Amplification

Amplification of a specific size class of the restricted DNA may be performed directly in the same hydrogel matrix in which the size classes have been separated in the device. In cases where more than species identification is necessary, electrophoresis first helps purify DNA from the total specimen. Then amplification before final DNA detection means that specificity of amplification is combined with specific electrophoretic mobility to make detection of signal stronger and thereby easier over background DNA.

EXAMPLE 14

Electrophoretic Separation, Amplification, and Hybridization

Hybridizing a labeled nucleic acid probe to nucleic acid targets produced as according to Example 13 is a way to determine the presence of specific DNA targets, thus reducing matrix background signal and simplifying software interpretation of the results.

EXAMPLE 15

Electrophoretic Separation Hybridization, and Amplification

Initial electrophoresis of nucleic acids as in Examples 11-14 may be followed by hybridization with one or more primary molecular probes, which are then amplified by one of the transcription-based methods such as the Q Beta replicase method (see Lizardi et al., cited in Example 9).

While the invention has been described in detail with respect to specific illustrative examples and embodiments, it will be apparent that numerous other variations, modifications, and embodiments are possible, and accordingly all such variations, modifications and embodiments are to be regarded as being within the spirit and scope of the invention. Such variations include, but are not limited to the detection of RNA or protein or other cellular components in the device using known detection methods and reagents.

What is claimed is:

1. A carrier device for specimen handling for analysis of a specimen for cellular components, comprising:

a top cover portion and a bottom housing portion, said top cover portion movable between an open and a closed position; said top cover portion having a first area that extends beyond a first side of said bottom housing portion;

said top cover portion and said bottom housing portion connected together by way of a hinge along one side of said bottom housing portion, wherein said top cover portion hingedly moves away from the bottom housing portion and upward from the closed position to an open position; and said bottom housing portion having edges on second and third sides and an extended area on a fourth side of said bottom housing portion extending beyond said top cover portion, said side edges defining a space called the matrix and specimen holding area; opposing surfaces of said top and bottom portions defining a top and bottom of said matrix and specimen holding area when said top cover portion is in a closed position; said space being in fluid communication with and extending to the extended area; said extended area containing a fluid receiving area; and wherein when said top cover portion is closed and aligned with respect to the side edges of the bottom housing portion, the top cover portion covers the matrix and specimen holding area, and fluids added to said fluid receiving area fill said matrix and specimen holding area; wherein excess fluids exit the matrix and specimen holding area at an end of the matrix and specimen holding area opposite the fluid receiving area.

2. A carrier device according to claim 1, wherein the top cover portion is hinged to the bottom housing portion along the first side of said bottom housing portion.

3. A carrier device according to claim 1, wherein the top cover portion is hinged to the bottom housing portion along second side of said bottom housing portion, and said second side is perpendicular to said first side of said bottom housing portion.

4. A carrier device according to claim 1, wherein the matrix and specimen holding area is divided into sections such that certain of the sections may be selected to individually treat specimens.

5. A carrier device according to claim 1, further comprising a matrix material containing a specimen in said matrix and specimen holding area; wherein fluids added to the fluid receiving area after the matrix material and specimen are in the matrix and specimen holding area form a liquid film in contact with the top cover portion and the matrix and specimen material when said top cover potion is in the closed position.

6. A carrier device according to claim 5, wherein said matrix material is selected from a group consisting of agarose and polyacrylamide.

7. A carrier device according to claim 6, wherein openings are positioned towards opposite ends of the carrier to allow wires to make electrical contact directly with the matrix material in the matrix and specimen holding area and indirectly through fluids in the fluid receiving area; wherein the carrier is structured so a current may be applied that permits electrophoretic transfer of macromolecules from one matrix section to another.

8. A carrier according to claim 5, wherein the carrier is made of material sufficient to withstand being heated and cooled rapidly by direct contact with a platform heater between temperatures required for melting agarose, rendering specimen non-infectious and denaturing DNA and temperatures required for complexation reactions within the specimen.

9. A carrier device according to claim 1, wherein the structure of the carrier allows fluids to behave so that the first fluid applied to fluid receiving area spreads into a liquid film over the matrix and specimen holding area; wherein a second fluid added to said fluid receiving area is capable of replacing first fluid in said fluid receiving area and the liquid film over the matrix and specimen holding area; wherein fluids added one after another flow through the carrier in one direction.

10. A carrier device according to claim 1, wherein at least one piece of said top and bottom portions is constructed of multiple pieces and at least one of the pieces is made of an optically clear material.

11. A carrier device according to claim 1, wherein each of a plurality of said carrier devices has structures for placing them together within a processor-controlled apparatus.

12. A carrier device for specimen handling for analysis of a specimen for cellular components, comprising:

a top cover portion and a bottom housing portion movable between an open position and a closed position, said bottom housing portion having an extended area on a first side of said bottom housing portion extending beyond said top cover portion; wherein said bottom housing portion has edges defining a space, said space comprises a fluid receiving area in the extended area and a matrix and specimen holding area; said fluid receiving area being in fluid communication with said matrix and specimen holding area; wherein a matrix and a specimen may be added to the matrix and specimen holding area; wherein the top cover portion covers said matrix and specimen holding area when said top cover portion is in the closed position; and wherein fluids added to said fluid receiving area fill said matrix and specimen holding area forming a liquid film in contact with the top cover portion and the matrix and specimen; wherein excess fluids exit the matrix and specimen holding area opposite where the fluids are added.

* * * * *